US011832065B2

(12) United States Patent
Furman et al.

(10) Patent No.: US 11,832,065 B2
(45) Date of Patent: Nov. 28, 2023

(54) HAPTIC TINNITUS THERAPEUTIC SYSTEM

(71) Applicant: Bose Corporation, Framingham, MA (US)

(72) Inventors: Adam Charles Furman, Bolton, MA (US); Andrew Todd Sabin, Chicago, IL (US); William M. Rabinowitz, Bedford, MA (US); Keith Dana Martin, Westborough, MA (US); John Andrew Trotter, Sudbury, MA (US)

(73) Assignee: Bose Corporation, Framingham, MA (US)

( * ) Notice: Subject to any disclaimer, the term of this patent is extended or adjusted under 35 U.S.C. 154(b) by 72 days.

(21) Appl. No.: 17/355,440

(22) Filed: Jun. 23, 2021

(65) Prior Publication Data

US 2021/0400407 A1 Dec. 23, 2021

Related U.S. Application Data

(60) Provisional application No. 63/042,606, filed on Jun. 23, 2020.

(51) Int. Cl.
*H04R 25/00* (2006.01)
*A61M 21/00* (2006.01)

(52) U.S. Cl.
CPC ............ *H04R 25/75* (2013.01); *A61M 21/00* (2013.01); *H04R 25/606* (2013.01); *A61M 2021/0022* (2013.01); *A61M 2021/0027* (2013.01); *A61M 2209/088* (2013.01); *A61M 2210/0662* (2013.01); *H04R 2460/13* (2013.01)

(58) Field of Classification Search
CPC .... A61M 21/00–02; A61M 2021/0022; H04R 25/75
See application file for complete search history.

(56) References Cited

U.S. PATENT DOCUMENTS 7,613,519 B2 11/2009 De Ridder
8,262,717 B2 9/2012 Rogers et al.
(Continued)

FOREIGN PATENT DOCUMENTS

WO WO-2015028480 A1 * 3/2015 ............ H04R 25/75
WO 2016/176668 A1 11/2016
(Continued)

OTHER PUBLICATIONS

PCT International Search Report and Written Opinion for International Application No. PCT/US2021/038589, dated Nov. 19, 2021, 22 pages.
(Continued)

*Primary Examiner* — Thaddeus B Cox
(74) *Attorney, Agent, or Firm* — Hoffman Warnick LLC (57) ABSTRACT

Various aspects include approaches for managing tinnitus in a user. In some particular aspects, a computer-implemented method of managing tinnitus of a user with at least one wearable device includes: actuating, according to a prescribed pattern and using the at least one wearable device: a) an electro-acoustic transducer to provide an audio output to the user, and b) a contact element to apply vibration to a body part of the user, where the prescribed pattern both stimulates the nervous system of the user and delivers a sound to the user, which together mitigate the tinnitus.

17 Claims, 5 Drawing Sheets

(56) References Cited

U.S. PATENT DOCUMENTS

| | | |
|---|---|---|
| 8,506,469 B2 | 8/2013 | Dietrich et al. |
| 8,591,419 B2 | 11/2013 | Tyler |
| 8,885,861 B2 | 11/2014 | Beck et al. |
| 9,242,067 B2 | 1/2016 | Shore et al. |
| 9,682,232 B2 | 6/2017 | Shore et al. |
| 10,569,082 B2 | 2/2020 | Shore et al. |
| 2003/0195588 A1 | 10/2003 | Fischell et al. |
| 2011/0071340 A1* | 3/2011 | McGuire ............... A61M 21/00 600/28 |
| 2011/0130615 A1 | 6/2011 | Mishelevich |
| 2011/0178442 A1 | 7/2011 | Mishelevich |
| 2013/0066350 A1 | 3/2013 | Mishelevich |
| 2014/0126752 A1* | 5/2014 | Beck ................. A61N 1/36036 381/151 |
| 2015/0126802 A1 | 5/2015 | Lim et al. |
| 2017/0151436 A1 | 6/2017 | Flaherty et al. |
| 2018/0169411 A1 | 6/2018 | Goodall et al. |
| 2018/0169412 A1 | 6/2018 | Goodall et al. |
| 2019/0001117 A1 | 1/2019 | Ben-David et al. |
| 2019/0163952 A1* | 5/2019 | Mueller-Wehlau .... A61B 5/128 |
| 2019/0282808 A1 | 9/2019 | Lim et al. |
| 2019/0374427 A1* | 12/2019 | DiMino ............. A61H 23/0245 |

FOREIGN PATENT DOCUMENTS

| | | |
|---|---|---|
| WO | 2017/085083 A1 | 5/2017 |
| WO | 2018/111997 A2 | 6/2018 |
| WO | 2019/005774 A1 | 1/2019 |

OTHER PUBLICATIONS

Anonymous, Tinnitus masker, WikipediA, Feb. 5, 2020, pp. 1-5.

* cited by examiner

HAPTIC TINNITUS THERAPEUTIC SYSTEM

PRIORITY CLAIM

This application claims priority to U.S. Provisional Patent Application No. 63/042,606, filed on Jun. 23, 2020, which is incorporated by reference in its entirety.

TECHNICAL FIELD

This disclosure generally relates to tinnitus therapy. More particularly, the disclosure relates to systems and approaches for performing tinnitus therapy.

BACKGROUND

Tinnitus is the phantom perception of sound experienced in a subject's ear or head, when no actual sound is present. Tinnitus, considered a subjective phenomenon, can vary in degrees of severity. One commonly referred to expression of tinnitus is "ringing in the ears"; but there are many different forms of tinnitus. Unfortunately, conventional techniques for reducing tinnitus are inadequate.

SUMMARY

All examples and features mentioned below can be combined in any technically possible way.

Various implementations of the disclosure include systems and approaches for managing tinnitus in a user.

In some particular aspects, a computer-implemented method of managing tinnitus of a user with at least one wearable device includes: actuating, according to a prescribed pattern and using the at least one wearable device: a) an electro-acoustic transducer to provide an audio output to the user, and b) a contact element to apply vibration to a body part of the user, where the prescribed pattern both stimulates the nervous system (e.g., somatic and/or autonomic nervous systems) of the user and delivers a sound to the user, which together mitigate the tinnitus.

In additional particular aspects, a system for managing tinnitus of a user includes: at least one wearable device having: an electro-acoustic transducer configured to provide an audio output; a contact element configured to apply vibration to a body part of the user; and a controller configured to: actuate the electro-acoustic transducer and the contact element according to a prescribed pattern to stimulate the somatic nervous system (e.g., somatic and/or autonomic nervous systems) of the user and the auditory nervous system of the user, which together interact to mitigate the tinnitus.

In further particular aspects, a computer-implemented method of tuning a wearable audio device for managing tinnitus in a user includes: actuating an electro-acoustic transducer at the wearable audio device to output a set of tonal stimuli across a range of frequencies; prompting a user of the wearable audio device for feedback about a tinnitus response to the set of tonal stimuli; and defining tonal stimuli settings for the wearable audio device based on the feedback from the user.

In additional particular aspects, a computer-implemented method of managing tinnitus of a user with a wearable hearing assistance device includes: detecting ambient acoustic signals at the wearable hearing assistance device; and actuating an electro-acoustic transducer at the wearable hearing assistance device to provide an audio output of the ambient acoustic signals with a notch at a frequency range approximating a known frequency at which the user perceives tinnitus.

In other particular aspects, a wearable hearing assistance device for managing tinnitus of a user includes: at least one microphone for detecting ambient acoustic signals; an electro-acoustic transducer configured to provide an audio output; and a controller configured to actuate the electro-acoustic transducer to provide an audio output of the ambient acoustic signals with a notch at a frequency range approximating a known frequency at which the user perceives tinnitus.

Implementations may include one of the following features, or any combination thereof.

In certain implementations, the at least one wearable device includes a wearable audio device having both the electro-acoustic transducer and the contact element, where the method includes actuating the contact element to apply vibration to a head of the user.

In particular cases, the vibration is applied to at least one of: a temple region of the user, a bridge of a nose of the user, an ear region of the user, a scalp of the user, a nape of the user, or a neck of the user.

In some aspects, the vibration is applied to the ear region proximate the ear canal entrance or the cymba concha.

In particular implementations, the contact element includes a vibro-tactile actuator.

In certain cases, the at least one wearable device includes: a wearable audio device and an additional wearable device, where the wearable audio device includes a head-worn audio device and the additional wearable device includes at least one of: a smart watch, a smart ring, a smart phone, a smart back massager, a smart wristband, armband or ankle band, or a smart shoe insole, and the prescribed pattern is tailored to stimulate the somatic nervous system (e.g., somatic and/or autonomic nervous systems) with the vibration applied to a body part of the user that is remote from the ear of the user.

In some implementations, the tinnitus includes somatic tinnitus.

In particular cases, the tinnitus includes tonal tinnitus.

In certain aspects, the prescribed pattern includes temporally relating the audio output with the application of pressure.

In some cases, the prescribed pattern extends for at least two to three minutes per day.

In particular implementations, the prescribed pattern extends for at least 15 minutes per day.

In certain aspects, the prescribed pattern extends for approximately 5 minutes to approximately 45 minutes per day for at least two days per week.

In particular cases, the audio output is provided as at least one of: a) broadband sounds with a notch at a frequency range approximating a frequency at which the user perceives the tinnitus, b) broadband sounds with a peak at a frequency range approximating a frequency at which the user perceives the tinnitus, c) at least one tone at a frequency outside of the frequency range approximating the frequency at which the user perceives the tinnitus, or d) at least one tone at the frequency range approximating the frequency at which the user perceives the tinnitus.

In some implementations, the method further includes: outputting at least one of the set of tonal stimuli according to a prescribed pattern for identifying a frequency range at which the user perceives the tinnitus based on the feedback.

In certain cases, during actuation, each tonal stimulus in the set of tonal stimuli is repeated at least once.

In particular aspects, a plurality of tonal stimuli are output across a narrower range of frequencies according to the prescribed pattern.

In some implementations, the prescribed pattern includes repeating output of the plurality of tonal stimuli across the narrower range of frequencies.

In some aspects, the range of frequencies spans above and below a known frequency range approximating the frequency at which the user perceives the tinnitus.

In certain aspects, the set of tonal stimuli includes a quiet tone at a known frequency range approximating the frequency at which the user perceives the tinnitus.

In particular implementations, the frequency at which the user perceives the tinnitus includes a range of frequencies.

In certain cases, the wearable hearing assistance device acoustically seals an ear canal of the user to aid in blocking the ambient acoustic signals in the frequency range that approximates the known frequency at which the user perceives tinnitus.

In particular implementations, the audio output only permits hearthrough of frequencies outside of the frequency range approximating the known frequency at which the user perceives tinnitus.

In some aspects, the audio output further includes an active noise cancelation output with an equalization setting that reduces hearthrough of the frequencies in the frequency range approximating the known frequency at which the user perceives tinnitus.

In certain cases, the range of frequencies spans from approximately one-half of an octave below, to one-half of an octave above, the known frequency at which the user perceives tinnitus.

In particular implementations, the audio output is provided as broadband noise with the notch at the frequency range that approximates the known frequency at which the user perceives tinnitus.

Two or more features described in this disclosure, including those described in this summary section, may be combined to form implementations not specifically described herein.

The details of one or more implementations are set forth in the accompanying drawings and the description below. Other features, objects and advantages will be apparent from the description and drawings, and from the claims.

It is noted that the drawings of the various implementations are not necessarily to scale. The drawings are intended to depict only typical aspects of the disclosure, and therefore should not be considered as limiting the scope of the invention. In the drawings, like numbering represents like elements between the drawings.

DETAILED DESCRIPTION

As noted herein, various aspects of the disclosure generally relate to tinnitus therapy. More particularly, aspects of the disclosure relate to managing tinnitus in a user with at least one wearable device.

Commonly labeled components in the FIGURES are considered to be substantially equivalent components for the purposes of illustration, and redundant discussion of those components is omitted for clarity.

Aspects and implementations disclosed herein may be applicable to a wide variety of speaker systems, such as wearable audio devices in various form factors, such as headphones (whether on or off ear), headsets, watches, eyeglasses, neck-worn speakers, shoulder-worn speakers, body-worn speakers, audio sleeping aids, etc. Unless specified otherwise, the term wearable audio device, as used in this document, includes headphones and various other types of personal audio devices such as head, shoulder or body-worn acoustic devices that include one or more acoustic drivers to produce sound. Some particular aspects disclosed may be particularly applicable to personal (wearable) audio devices such as in-ear headphones (also referred to as earbuds), eyeglasses or other head-mounted audio devices.

While described by way of example, wearable audio devices such as in-ear headphones (e.g., earbuds), audio accessories or clothing (e.g., audio hats, audio visors, audio jewelry, neck-worn speakers or audio eyeglasses (also referred to as eyeglass headphones) herein, the wearable audio devices disclosed herein can include additional features and capabilities. That is, the wearable audio devices described according to various implementations can include features found in one or more other wearable electronic devices, such as smart glasses, smart watches, etc. These wearable audio devices can include additional hardware components, such as one or more cameras, location tracking devices, microphones, etc., and may be capable of voice recognition, visual recognition, and other smart device functions. The description of wearable audio devices included herein is not intended to exclude these additional capabilities in such a device.

Various implementations include systems and approaches for managing tinnitus in a user with a wearable device, e.g., a wearable audio device such as a wearable hearing assistance device, and/or an additional wearable device. In contrast to conventional approaches, the systems and approaches described according to various implementations combine audio stimulation with stimulation of one or more additional neural pathways in order to manage tinnitus. In certain additional implementations, approaches include defining tonal stimuli settings for a wearable audio device based on user testing and feedback. In still further implementations, approaches include controlling output of ambient acoustic signals (or, hearthrough) to provide a notch at a frequency range that approximates a user's known tinnitus percept frequency.

Figure 1:
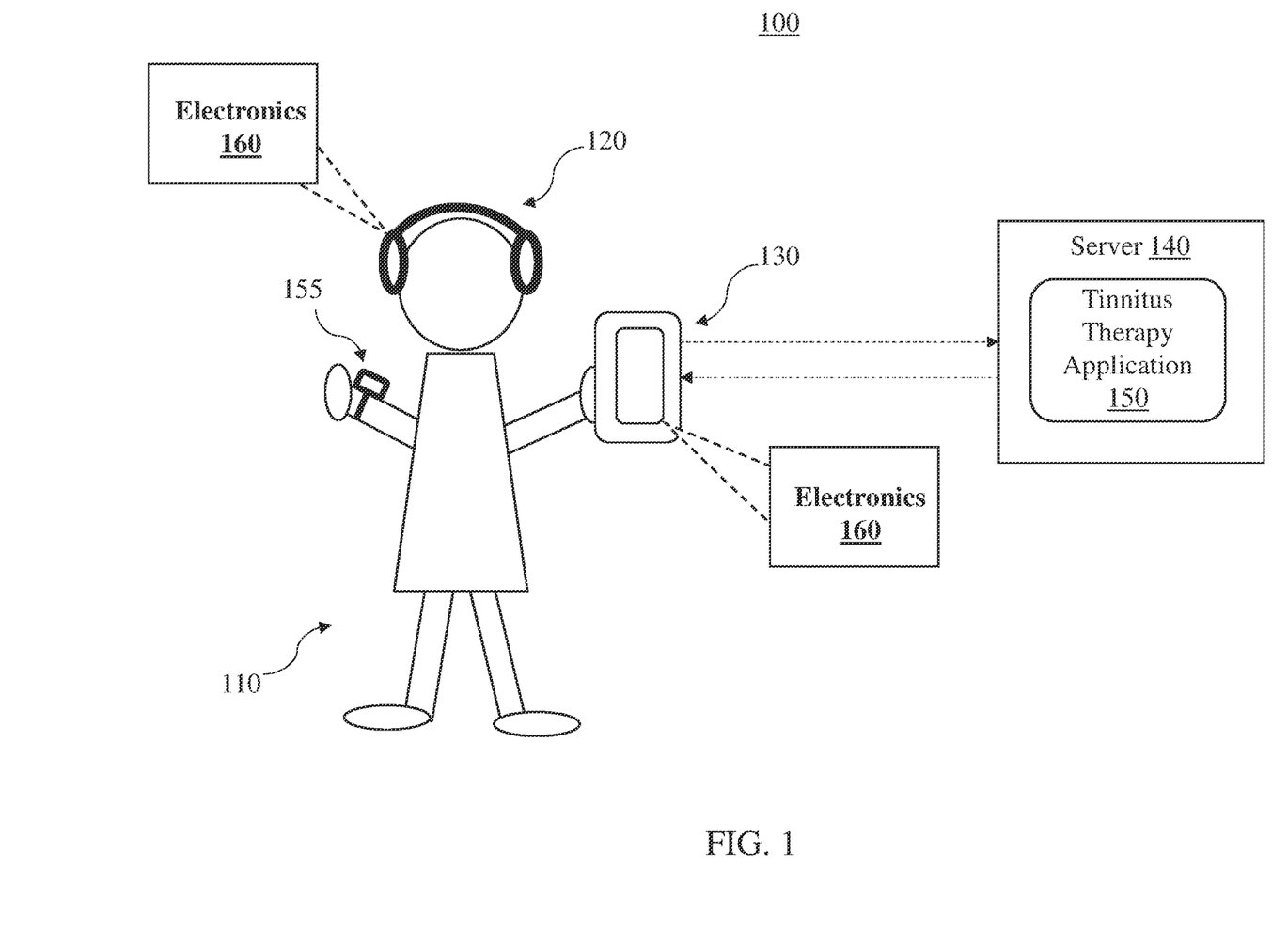
FIG. 1 shows an illustrative environment for performing tinnitus therapeutic functions according to various implementations.

FIG. 1 illustrates an example environment 100, including a user 110 and an audio device (e.g., a wearable audio device) 120. While the audio device 120 is illustrated in this example as a wearable audio device (e.g., headphones, earphones, audio glasses, open-ear audio devices, shoulder-worn speakers or wearable speakers), the audio device 120 can include any conventional portable audio device such as a portable speaker, portable smart speaker, etc. In some implementations, the audio device 120 is connected with an audio gateway 130. In various implementations, the audio gateway 130 includes a smart device, e.g., a portable smart device. In additional implementations, the audio device 120 can have integrated smart device capabilities (e.g., communications and data processing). Both the audio device 120 and the audio gateway 130 can include processing components and communications components, for communicating with one another and/or other devices in the environment 100. In certain cases, the communications components include one or more wireless transceivers, e.g., to communicate with one or more smart devices in the environment 100. The wireless transceivers can also be used to communicate with a server 140 hosting a mobile application that is running on the audio gateway 130 and/or the audio device 120, for example, a tinnitus therapy application 150. The server 140 can include a cloud-based server, a local server or any combination of local and distributed computing components capable of executing functions described herein. In various particular implementations, the server 140 is a cloud-based server configured to host the tinnitus therapy application 150, e.g., running on the audio gateway 130. According to some implementations, the tinnitus therapy application 150 is downloaded to the user's audio device 120 and/or audio gateway 130 in order to enable functions described herein. In certain cases, the server 140 is connected with a computing device that enables coding of the tinnitus therapy application 150, e.g., by a software developer or other programmer.

In certain implementations, the environment 100 can also include an additional wearable device 155 configured to aid in tinnitus management processes described herein. In some cases, the additional wearable device 155 includes one or more of the following: a smart watch; a smart ring; a smart phone; a smart back massager; a smart wrist, arm or ankle band; or a smart shoe insole. In the example depiction in FIG. 1, the wearable device 155 is shown as a smart watch or smart wristband or armband. In certain implementations, as noted herein, the audio device 120, audio gateway 130 and/or additional wearable device 155 includes a contact element to apply vibration to a body part of the user 110. In some cases, e.g., where the additional wearable device 155 is remote from the user's ear(s), the contact element at the additional wearable device 155 is configured to apply vibration to the remote body part of the user 110. According to various implementations, the vibration applied to one or more body parts of the user can include applying pressure such as a tap, bump, pulse, etc. in any pattern, including the static application of pressure.

Figure 2:
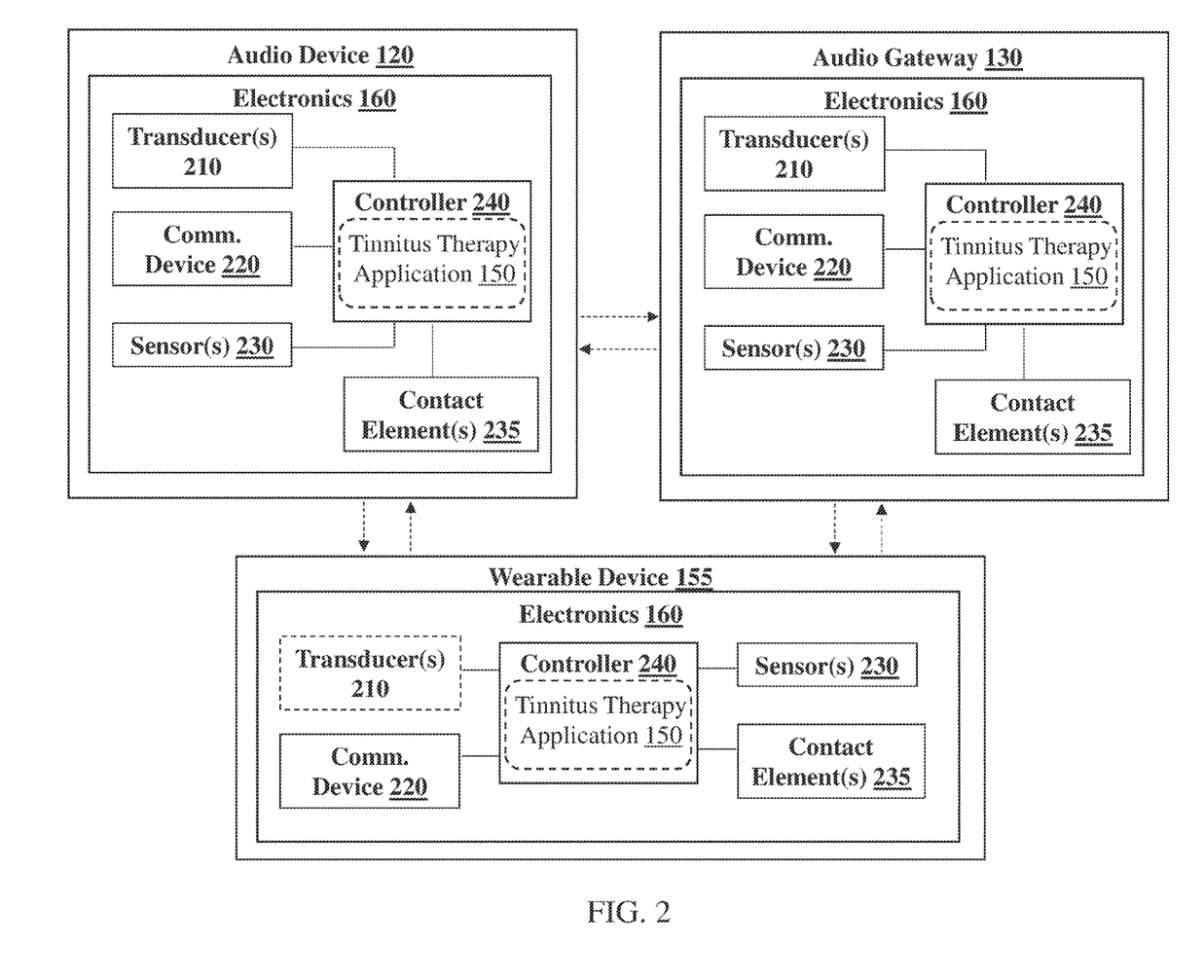
FIG. 2 is a schematic depiction of select electronics substantially contained in devices depicted in FIG. 1.

The audio device 120, audio gateway (e.g., smart device) 130 and/or additional wearable device 155 can each include various electronics 160, illustrated in simplified form in the system diagram in FIG. 2. For example, electronics 160 can include transducers 210 (e.g., at least one electroacoustic transducer for producing an acoustic output), communications (comm.) devices 220 (e.g., wireless transceivers), a set of sensors 230 (e.g., optical sensor(s), acoustic sensors (e.g., microphone array(s)), MEMS devices that combines a multi-axis accelerometer, gyroscope, and/or magnetometer (sometimes referred to as an IMU or inertial measurement unit), etc.), and one or more contact elements 235 (e.g., vibro-tactile actuators, transducers, piezoelectric devices, gyroscopic components, etc. In some implementations, the additional wearable device 155 is part of the audio gateway 130 (e.g., smart device), such that one or more functions described with reference to these devices is performed at the same device. Components in electronics 160 can be connected or otherwise centrally managed by a controller 240.

In various implementations, the controller 240 in the audio device 120, the audio gateway 130 and/or the wearable device 155 can include a processor (e.g., including a logic engine) to execute instructions for controlling device functions, e.g., to manage or otherwise treat tinnitus in the user 110. In some cases, a memory is coupled with the processor to store the instructions. In other implementations, the processor can otherwise access the instructions, e.g., from a remote storage system such as the server 140 (FIG. 1). When executed by the processor in the controller 240, the instructions cause the processor to perform a tinnitus management approach, test the user 110 (FIG. 1) for tinnitus response(s) and define corresponding tonal stimuli to manage tinnitus, and/or control ambient audio hearthrough to manage tinnitus for the user 110. In some cases, the instructions are part of the tinnitus therapy application 150, which can be accessed via the server 140 or locally stored in memory, e.g., at the controller 240 or in another storage system in the audio device 120, the audio gateway 130 and/or the wearable device 155. The memory at the audio device 120 and/or the audio gateway 130 can include, for example, flash memory and/or non-volatile random access memory (NVRAM). In some implementations, instructions (e.g., software such as the tinnitus therapy application 150) are stored in an information carrier. The instructions, when executed by one or more processing devices, perform one or more processes, such as those described elsewhere herein. The instructions can also be stored by one or more storage devices, such as one or more (e.g. non-transitory) computer- or machine-readable mediums (for example, the memory, or memory on the processor). As described herein, the memory can include instructions, or the processor can otherwise access instructions for taking a prescribed action according to various particular implementations. It is understood that portions of the memory (e.g., instructions) can also be stored in a remote location or in a distributed location, and can be fetched or otherwise obtained by the processor (e.g., via any communications protocol described herein) for execution.

Additional components included in electronics 160 and not necessarily depicted can include power source(s), signal amplification and other digital signal processing (DSP) hardware and/or software, active noise reduction (ANR) and/or controllable noise cancelling (CNC) systems, input/output (I/O) devices, displays and/or user interfaces (UIs), etc. It is understood that the electronics 160 at the audio gateway 130 and/or additional wearable device 155 can include various additional components not included at the audio device 120, for example, components enabling smart device functions, audio gateway functions and additional processing.

In any case, the controller 240 is configured to aid in managing and/or treating tinnitus in the user 110 (FIG. 1) according to one or more approaches described herein. In certain implementations, approaches are particularly suited for treating tonal tinnitus, i.e., the perception of overlapping sounds or near-continuous sound with a well-defined frequency, such as ringing, whistling, or buzzing. Other approaches are particularly suited for treating non-tonal (e.g., somatic) tinnitus, which is the perception of sounds associated with tonal tinnitus that are cause or modified by the sensory system in the body, e.g., muscle spasms, pressure in the dental cavities such as impacted teeth, etc.

Figure 3:
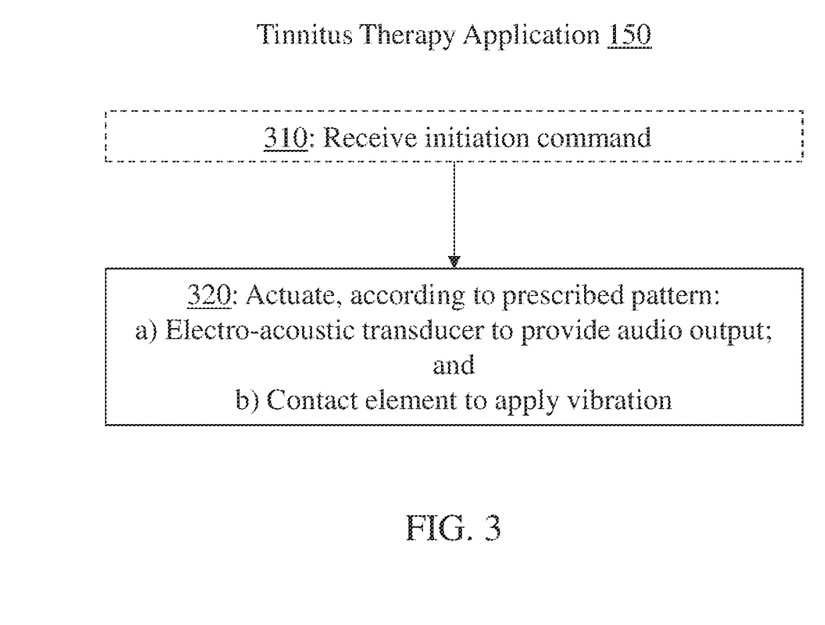
FIG. 3 is a flow diagram illustrating a method performed by a tinnitus therapy application according to various implementations.
Figure 4:
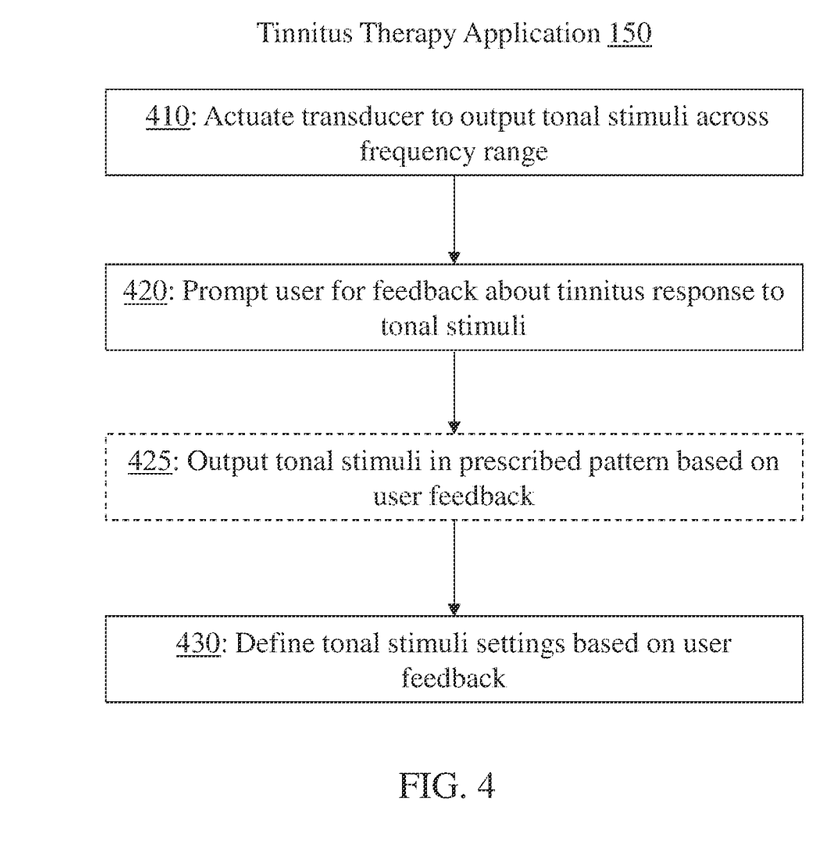
FIG. 4 is a flow diagram illustrating an additional method performed by a tinnitus therapy application according to various implementations.
Figure 5:
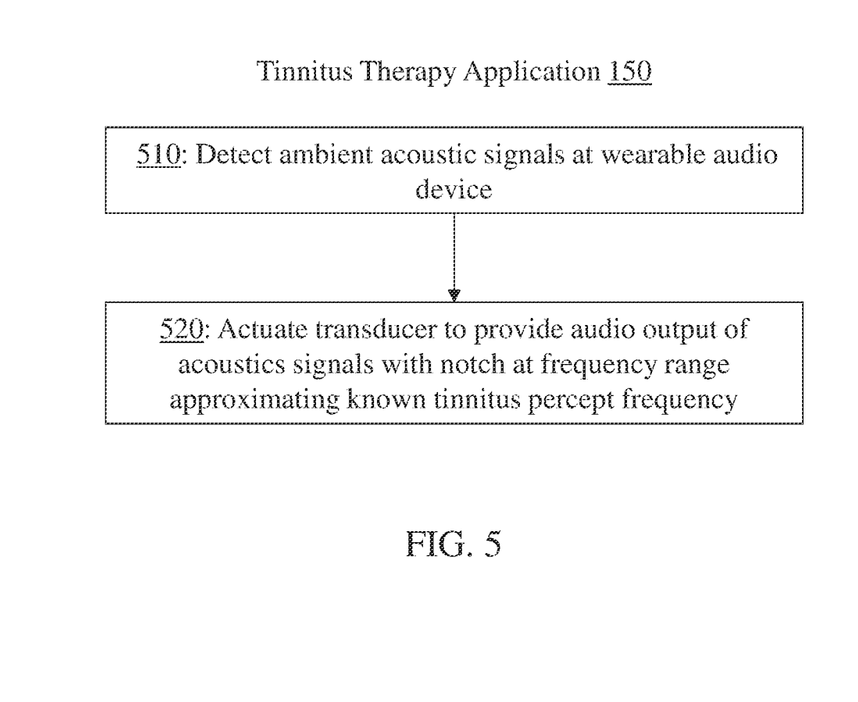
FIG. 5 is a flow diagram illustrating a further method performed by a tinnitus therapy application according to various implementations.

In any case, as noted herein, the controller 240 is configured to aid in managing and/or treating tinnitus (e.g., tonal and/or non-tonal tinnitus) in the user 110. FIGS. 3-5 are flow diagrams illustrating processes in methods performed according to various implementations. In certain implementations, processes in the flow diagrams are performed by the tinnitus therapy application 150 running at one or more devices described herein. These processes are described with continuing reference to FIGS. 1 and 2. In some cases, as described herein, processes shown sequentially can be performed simultaneously, or nearly simultaneously. However, in other cases, these processes can be performed in a different order.

Turning to FIG. 3, in some implementations, the controller 240 is configured (in an optional pre-process) to receive an initiation command to run the tinnitus therapy application 150 (process 310). In certain cases, this initiation command can be from the user 110 (e.g., at an interface on the wearable audio device 120, audio gateway 130 and/or additional wearable device 155). In other cases, the initiation command can be triggered by the tinnitus therapy application 150, e.g., in response to a detected time or day of the week, a setting specific to the user, and/or an input from the sensor(s) 230. In some cases, the tinnitus therapy application 150 is triggered to run in response to detected adjustment of one or more settings on the audio device 120, e.g., by user 110.

In any case, in response to initiation of the tinnitus therapy application 150, the controller 240 is configured (in process 320) to actuate, according to a prescribed pattern using a wearable device (e.g., wearable audio device 120 and/or additional wearable device 155): a) electro-acoustic transducer (s) 210 to provide an audio output to user 110; and b) contact element 235 to apply vibration to a body part of the user 110. In some cases, the output at the transducer 210 is provided at the wearable audio device 120, e.g., when the user is wearing headphones, earphones, or other personal audio devices. In other cases, the output at the transducer 210 is provided at the audio gateway 130 and/or the additional wearable device 155. In certain implementations, the tinnitus therapy application 150 is configured to control actuation of the contact element 235 at a device that is distinct from the wearable audio device 120, e.g., at the additional wearable device 155 and/or the audio gateway 130. In these cases, the vibration is applied to a body part that is remote from the user's ear. In certain examples, the prescribed treatment pattern, e.g., applying the vibration to a body part that is remote from the user's ear, is tailored to stimulate the nervous system of the user 110 (e.g., the somatic nervous system). These example implementations can be tailored to treat somatic tinnitus.

In other implementations, the tinnitus therapy application 150 is configured to control actuation of the contact element 235 on the audio device 120, such that process 320 includes actuating the contact element 235 to apply the vibration to the head of the user 110. In certain of these cases, the vibration is applied to one or more regions of the head of the user 110, e.g., to the temple region(s), the bridge of the nose, the ear region(s), the scalp, the nape, and/or the neck of the user 110. In some cases, the tinnitus therapy application 150 is configured to vary the vibration pattern based on the location of the application on the user's head. According to particular implementations, distinct forms of audio device 120 are configured to apply vibration to different regions of the head of the user 110, e.g., such that an over-ear headphone can apply vibration to one or more regions proximate the user's ears (e.g., temple region) and/or proximate a headband, while an in-ear headphone such as an earbud can apply pressure in a more localized region of the user's ears, and audio eyeglasses can apply pressure in regions proximate the user's ears as well as across the bridge of the nose, the temple region, etc. In one particular example, the tinnitus therapy application 150 is configured to initiate vibration at the audio device 120, in particular, to apply vibration to the ear region of the user proximate the ear canal entrance or the cymba concha. In these examples, application of vibration proximate the ear canal entrance or the cymba concha can be beneficial because the vagus nerve innervates those regions. Stimulating the vagus nerve can induce neural plasticity.

In various implementations, the tinnitus therapy application 150 initiates the audio output (e.g., at transducer(s) 210, such as transducers at the audio device 120) as: a) broadband sounds with a notch at a frequency range approximating a frequency at which the user perceives the tinnitus; b) broadband sounds with a peak at a frequency range approximating a frequency at which the user perceives the tinnitus; c) at least one tone (e.g., a soft tone) at a frequency outside of the frequency range approximating the frequency at which the user perceives the tinnitus; and/or d) at least one tone at the frequency range approximating the frequency at which the user perceives the tinnitus (e.g., as detected by feedback from the user 110).

As noted herein, the tinnitus therapy application 150 is configured to actuate both the transducer(s) 210 and the contact element(s) 235 according to a prescribed pattern in order to treat or otherwise manage tinnitus in the user 110. In particular implementations, the prescribed pattern includes temporally relating the audio output at the transducer(s) 210 with the application of pressure at the contact element(s) 235. That is, the treatment pattern is applied at a prescribed temporal relationship between audio and pressure. According to implementations, a variety of distinct treatment patterns are possible to manage distinct types of tinnitus (e.g., tonal versus non-tonal), as well as distinct sub-types of tinnitus as perceived by the user 110. In certain examples, the prescribed pattern extends for at least two to three minutes per day, for one or more days per week. In some examples, the prescribed pattern extends for at least two to three minutes per day for at least two days per week. In particular examples, the prescribed pattern extends for at least two to three minutes per day for at least three to four days per week. In certain cases, the prescribed pattern extends for one or more weeks, e.g., up to several weeks or until the user 110 exhibits an acceptable reduction in the perception of tinnitus. In certain examples, the prescribed pattern extends for at least 15 minutes per day, e.g., for one or more days per week. In some additional examples, the prescribed period extends for approximately 5 minutes to approximately 45 minutes per day for at least two days per week (e.g., 3-4 days per week). The term "approximately" as used with respect to values herein can allot for a nominal variation from absolute values, e.g., of several percent or less.

FIG. 4 is a flow diagram illustrating processes performed by the tinnitus therapy application 150 in defining tonal stimuli settings for an audio device (e.g., audio device 120, FIG. 1) based on user feedback. In certain cases, the prescribed treatment pattern is controlled by the tonal stimuli settings. As such, the processes outlined in FIG. 4 can occur prior to processes described with reference to FIG. 3. As shown, process 410 can include actuating the transducer(s) 210 at the wearable audio device 120 to output a set of tonal stimuli across a range of frequencies. In certain cases, the set of tonal stimuli includes narrow band noise. After actuating the transducer(s) 210 to output the set of tonal stimuli, the tinnitus therapy application 150 is configured to prompt the user 110 for feedback about a tinnitus response to that stimuli (process 420). Based on the user feedback, the tinnitus therapy application 150 is configured to define tonal stimuli settings for the audio device 120 (process 430). In an intermediate process (shown optionally as process 425), the tinnitus therapy application 150 outputs the set of tonal stimuli according to a prescribed pattern (e.g., as described herein) for identifying a frequency range at which the user 110 perceives the tinnitus, based on the feedback received in response to the prompt.

According to some implementations, each tonal stimulus in the set is repeated at least once, e.g., to allow the user 110 to identify a best-fit tonal stimulus or group of best-fit tonal stimuli that effectively mitigate her perceived tinnitus. In some cases, when outputting the tonal stimuli according to a prescribed pattern, the tinnitus therapy application 150 is configured to output the tonal stimuli across a narrower range of frequencies with each progression in the pattern or each repetition of the pattern. That is, in some cases, the tinnitus therapy application 150 is configured to output tonal stimuli in a pattern that includes a progressively narrower range of frequencies. In certain cases, this progression from wider to narrower frequency ranges is repeated according to the prescribed pattern, e.g., the tinnitus therapy application 150 output's the tonal stimuli across a wider frequency range that progressively narrows until the pattern resets or restarts. In certain implementations, the range of frequencies at which the tinnitus therapy application 150 provides the audio output spans above and below a known frequency range at which the user 110 perceives the tinnitus. That is, in some cases, the tinnitus therapy application 150 provides the audio output across a frequency range that is known to span above and below the user's tinnitus percept frequency. In certain cases, the approximate tinnitus percept frequency is known ahead of time, e.g., due to prior testing with the user 110 or based on a data input from one or more of the sensors 230 that indicates the user 110 adjusts audio settings in response to particular frequencies of output. In other cases, the approximate tinnitus percept frequency for the user 110 is not necessarily known a priori, but instead, the tinnitus therapy application 150 outputs the set of tonal stimuli across a frequency range that is known to define an outer bound of tinnitus percept frequencies of a group of users, e.g., a general population of users or a population of users known to experience tinnitus, for example, as determined by empirical data. In certain cases, the tinnitus therapy application 150 outputs the tonal stimuli across the full range of hearing.

In certain cases, the user's tinnitus percept frequency includes a number of different frequencies. In other cases, the user's tinnitus percept frequency includes a broadband range of frequencies. In particular examples, the percept frequency/frequencies can exist anywhere within the range of human hearing.

In still further implementations, the tinnitus therapy application 150 is configured to manage tinnitus for the user 110 according to additional methods. FIG. 5 illustrates processes in an additional method of managing user tinnitus, e.g., by controlling hearthrough of ambient acoustic signals. Certain of these processes are applicable to audio devices 120 that have passive noise cancelation (PNR) or otherwise occlude the ear canal of the user. Additionally, certain of these processes are applicable to audio devices 120 that have both PNR and active noise reduction (ANR) or active noise cancelation (ANC) technology. Turning to FIG. 5, the tinnitus therapy application 150, when running, is configured to detect ambient acoustic signals at the audio device 120, e.g., with sensors 230 such as one or more microphones (process 510). In some cases, the ambient acoustic signals are detected with a microphone array including one or more feedforward and/or feedback microphones. In response to detecting the ambient acoustic signals, the tinnitus therapy application 150 is configured to actuate the transducer(s) 210 to provide a processed audio output (e.g., using ANR and/or ANC circuitry and/or digital signal processing) of the ambient acoustic signals with a notch at a frequency range that approximates a known tinnitus percept frequency for the user 110 (process 520). The known tinnitus percept frequency can be determined according to any approach described herein.

In certain cases, as noted herein, the audio device 120 acoustically seals an ear canal of the user 110 to aid in blocking the ambient acoustic signals in the frequency range that approximates the known tinnitus percept frequency for the user 110. In certain cases, the audio output at the transducer(s) 210 only permits hearthrough of frequencies that are outside of the frequency range that approximates the user's known tinnitus percept frequency. In cases where the audio device 120 has ANR/ANC capabilities, the tinnitus therapy application 150 is configured to initiate an ANR or ANC output according to an equalization setting that reduces hearthrough of frequencies in the range that approximates the known tinnitus percept frequency for the user 110. In certain cases, the range of frequencies approximating the known tinnitus percept frequency spans approximately one-half of an octave below, to one-half of an octave above, the known frequency at which the user perceives tinnitus. According to some implementations, the audio output is provided as broadband noise with a notch at the frequency range that approximates the known tinnitus percept frequency for the user 110.

In various particular implementations, the tinnitus therapy application 150 is configured to run on only one of the audio device 120 or the audio gateway 130 (e.g., in a respective controller 240). In these cases, the tinnitus therapy application 150 receives sensor data from sensors 230 at the device on which it is running (e.g., audio device 120), as well as from sensors 230 at the other device (e.g., audio gateway 130), for example, via any communications protocol described herein. In certain cases, the tinnitus therapy application 150 requires only limited processing resources, and as such, can be run on a single device such as the audio device 120 or the additional device 155.

In any case, the tinnitus therapy application 150 is configured to aid in treating and/or managing tinnitus for a user (e.g., user 110). That is, the technical effect of the tinnitus therapy application 150 is to control audio output functions in order to mitigate the effects of tinnitus on a user. As such, the tinnitus therapy application 150 can improve user experiences as well as health outcomes when compared with conventional tinnitus therapies and related systems.

The functionality described herein, or portions thereof, and its various modifications (hereinafter "the functions") can be implemented, at least in part, via a computer program product, e.g., a computer program tangibly embodied in an information carrier, such as one or more non-transitory machine-readable media, for execution by, or to control the operation of, one or more data processing apparatus, e.g., a programmable processor, a computer, multiple computers, and/or programmable logic components.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Actions associated with implementing all or part of the functions can be performed by one or more programmable processors executing one or more computer programs to perform the functions of the calibration process. All or part of the functions can be implemented as, special purpose logic circuitry, e.g., an FPGA and/or an ASIC (application-specific integrated circuit). Processors suitable for the execution of a computer program include, by way of example, both general and special purpose microprocessors, and any one or more processors of any kind of digital computer. Generally, a processor will receive instructions and data from a read-only memory or a random access memory or both. Components of a computer include a processor for executing instructions and one or more memory devices for storing instructions and data.

Elements of figures are shown and described as discrete elements in a block diagram. These may be implemented as one or more of analog circuitry or digital circuitry. Alternatively, or additionally, they may be implemented with one or more microprocessors executing software instructions. The software instructions can include digital signal processing instructions. Operations may be performed by analog circuitry or by a microprocessor executing software that performs the equivalent of the analog operation. Signal lines may be implemented as discrete analog or digital signal lines, as a discrete digital signal line with appropriate signal processing that is able to process separate signals, and/or as elements of a wireless communication system.

When processes are represented or implied in the block diagram, the steps may be performed by one element or a plurality of elements. The steps may be performed together or at different times. The elements that perform the activities may be physically the same or proximate one another, or may be physically separate. One element may perform the actions of more than one block. Audio signals may be encoded or not, and may be transmitted in either digital or analog form. Conventional audio signal processing equipment and operations are in some cases omitted from the drawings.

In various implementations, electronic components described as being "coupled" can be linked via conventional hard-wired and/or wireless means such that these electronic components can communicate data with one another. Additionally, sub-components within a given component can be considered to be linked via conventional pathways, which may not necessarily be illustrated.

Other embodiments not specifically described herein are also within the scope of the following claims. Elements of different implementations described herein may be combined to form other embodiments not specifically set forth above. Elements may be left out of the structures described herein without adversely affecting their operation. Furthermore, various separate elements may be combined into one or more individual elements to perform the functions described herein.

We claim:

1. A computer-implemented method of managing tinnitus of a user with a wearable audio device, the method comprising:
   actuating, according to a prescribed pattern and using the wearable audio device:
   a) an electro-acoustic transducer to provide an audio output to the user, and
   b) a contact element to apply vibration to a body part of the user,
   wherein the electro-acoustic transducer and the contact element are both located at the wearable audio device,
   wherein the prescribed pattern both stimulates the nervous system of the user and delivers a sound to the user, which together mitigate the tinnitus,
   wherein the wearable audio device acoustically seals an ear canal of the user, and wherein while managing the tinnitus of the user, the electro-acoustic transducer provides hearthrough of environmental sound in only frequencies outside of a frequency range approximating a frequency at which the user perceives the tinnitus.

2. The computer-implemented method of claim 1, wherein the method comprises actuating the contact element to apply vibration to a head of the user proximate to at least one of a temple region of the user, or an ear region of the user.

3. The computer-implemented method of claim 2, wherein the vibration is applied to the ear region proximate an ear canal entrance or a cymba concha.

4. The computer-implemented method of claim 1, wherein the contact element comprises a vibro-tactile actuator.

5. The computer-implemented method of claim 1, wherein the tinnitus comprises somatic tinnitus or tonal tinnitus.

6. The computer-implemented method of claim 1, wherein the prescribed pattern comprises temporally relating the audio output with the application of vibration.

7. The computer-implemented method of claim 6, wherein the prescribed pattern extends for:
   at least two to three minutes per day.

8. The computer-implemented method of claim 6, wherein the prescribed pattern extends for at least 15 minutes per day.

9. The computer-implemented method of claim 6, wherein the prescribed pattern extends for:
   approximately 5 minutes to approximately 45 minutes per day for at least two days per week.

10. The computer-implemented method of claim 1, wherein the audio output is provided as broadband sounds with a notch at a frequency range approximating the frequency at which the user perceives the tinnitus.

11. The computer-implemented method of claim 1, wherein the audio output is provided as broadband sounds with a peak at a frequency range approximating the frequency at which the user perceives the tinnitus.

12. The computer-implemented method of claim 1, wherein the audio output is provided as at least one tone at a frequency outside of a frequency range approximating the frequency at which the user perceives the tinnitus.

13. The computer-implemented method of claim 1, wherein the audio output is provided as at least one tone at a frequency range approximating the frequency at which the user perceives the tinnitus.

14. The computer-implemented method of claim 1, wherein the frequency range is approximately one-half of an octave below, to one-half of an octave above, the frequency at which the user perceives the tinnitus.

15. A computer-implemented method of managing tinnitus of a user with a set of wearable devices, the method comprising:
   actuating, according to a prescribed pattern and using the set of wearable devices:
   a) an electro-acoustic transducer to provide an audio output to the user, and
   b) a contact element to apply vibration to a body part of the user,
   wherein the set of wearable devices includes a wearable audio device and an additional wearable device, wherein the wearable audio device comprises a head-worn audio device and wherein the additional wearable device comprises at least one of: a smart watch, a smart ring, a smart phone, a smart back massager, a smart wrist, arm or ankle band, or a smart shoe insole, wherein the prescribed pattern both stimulates the nervous system of the user and delivers a sound to the user, which together mitigate the tinnitus, wherein the prescribed pattern is tailored to stimulate the nervous system with the vibration applied to a body part of the user that is remote from the ear of the user, and wherein the actuating according to the prescribed pattern is controlled by an application running on only one of the set of wearable devices, wherein the wearable audio device acoustically seals an ear canal of the user, and wherein while managing the tinnitus of the user, the electro-acoustic transducer provides hearthrough of environmental sound in only frequencies outside of a frequency range approximating a frequency at which the user perceives the tinnitus.

16. The computer-implemented method of claim 15, wherein the audio output is provided as broadband sounds with a peak at a frequency range approximating a frequency at which the user perceives the tinnitus.

17. The computer-implemented method of claim 15, wherein the audio output is provided as at least one tone at a frequency outside of a frequency range approximating a frequency at which the user perceives the tinnitus.

* * * * *